(12) United States Patent
Ouchi

(10) Patent No.: US 6,471,690 B1
(45) Date of Patent: Oct. 29, 2002

(54) CONNECTING PART IN ENDOSCOPIC TREATING INSTRUMENT

(75) Inventor: Teruo Ouchi, Saitama (JP)

(73) Assignee: Asahi Kogaku Kogyo Kabushiki Kaisha, Tokyo (JP)

(*) Notice: Subject to any disclaimer, the term of this patent is extended or adjusted under 35 U.S.C. 154(b) by 183 days.

(21) Appl. No.: 09/618,050

(22) Filed: Jul. 17, 2000

(30) Foreign Application Priority Data

Aug. 4, 1999 (JP) .......................................... 11-221130

(51) Int. Cl.[7] .............................................. A61B 17/00
(52) U.S. Cl. .............................. 606/1; 606/114; 600/121
(58) Field of Search .............................. 606/1, 113, 114, 606/146; 600/108, 121

(56) References Cited

U.S. PATENT DOCUMENTS 4,607,620 A * 8/1986 Storz ............................. 128/4
5,766,184 A * 6/1998 Matsuno et al. ............. 606/142
6,113,586 A * 9/2000 Ouchi ............................. 606/1
6,261,284 B1 * 7/2001 Ouchi ............................. 606/1

FOREIGN PATENT DOCUMENTS

| JP | 58160010 | 10/1983 | |
| JP | 60-31684 | 9/1985 | |
| JP | 61-4326 | 2/1986 | |
| JP | 63-65852 | 3/1988 | |
| JP | 110277047 A | * 10/1998 | ........... A61B/17/28 |
| JP | 11164836 A | * 6/1999 | ........... A61B/17/22 |

* cited by examiner

Primary Examiner—Denise L. Esquivel
Assistant Examiner—Marc Norman
(74) Attorney, Agent, or Firm—Greenblum & Bernstein, P.L.C.

(57) ABSTRACT

In a connecting part in an endoscopic treating instrument, there is provided, between a base end of a flexible sheath (10) and an operating member (34, 38), a reinforcing cover (40) into which an operation wire (20) is loosely inserted. The reinforcing cover (40) prevents a bending of the operation wire (20), and is detachable from the operation wire (20).

7 Claims, 3 Drawing Sheets

CONNECTING PART IN ENDOSCOPIC TREATING INSTRUMENT

BACKGROUND OF THE INVENTION

The present invention relates to a connecting part between an operation wire and an operating section in an endoscopic treating instrument.

Generally, the endoscopic treating instrument is so constructed that a flexible sheath into which an operation wire is inserted movably in an axial direction is connected to the operating section at its base end, and a base end of the operation wire is connected to an operating member that is movably arranged in the operating section to correspond to the moving direction of the operation wire.

The operation wire is fixedly covered with a reinforcing metal pipe at its rearward portion so that the operation wire may not be bent at a portion where it is exposed from the flexible sheath, when the operation wire is pushed into the flexible sheath with the operating member.

Some endoscopic treating instruments are available, which is designed so that the flexible sheath side and the operating section side are detachable from each other. In many cases of this type, the operation wire is removable from the flexible sheath in order to enable cleaning of an interior of the flexible sheath or so, after use.

However, the reinforcing metal pipe which is fixed to cover the base end portion of the operation wire is straight and long. Accordingly, when the operation wire which has been removed from the flexible sheath is inserted again into the flexible sheath, the flexible sheath must be straightened in order that the reinforcing metal pipe can be passed through the flexible sheath. This work is troublesome, and sometimes causes the reinforcing metal pipe to be broken by handling error.

SUMMARY OF THE INVENTION

In view of the above, an object of the invention is to provide a connecting part in an endoscopic treating instrument, which can, not only prevent an operation wire from being bent at the rearward portion, but also facilitate an insertion work of the operation wire into the flexible sheath.

A connecting part in an endoscopic treating instrument according to the invention is provided with a reinforcing cover into which an operation wire is loosely inserted and that is disposed between the base end of a flexible sheath and an operating member in detachable manner with respect to the operation wire. Therefore, not only the operation wire is prevented from being bent at the rearward portion, but the insertion work of the operation wire can be easily conducted without any trouble, when the operation wire which has been removed from the flexible sheath for cleaning and sterilizing purpose is inserted into the flexible sheath again for reassembling.

A connecting part in an endoscopic treating instrument according to a preferred embodiment of the invention includes: an operation wire; a flexible sheath into which the operation wire is inserted axially movably, the flexible sheath being removable from the operation wire; an operating section having a main body to which a base end of the flexible sheath is detachably connected, and an operating member arranged movably with respect to the main body, a base end of the operation wire being detachably connected to the operating member; and a reinforcing cover into which the operation wire is loosely inserted and that prevents bending of the operation wire. The reinforcing cover is preferably provided between the base end of the flexible sheath and the operating member and detachable from the operation wire.

One end of the reinforcing cover may be connected to the operating member, and further, a second reinforcing cover may be additionally provided, which is connected to the main body.

The present disclosure relates to the subject matter contained in Japanese patent application No. Hei. 11-221130 (filed on Aug. 4, 1999), which is expressly incorporated herein by reference in its entirety.

DESCRIPTION OF THE PREFERRED EMBODIMENT

Figure 1:
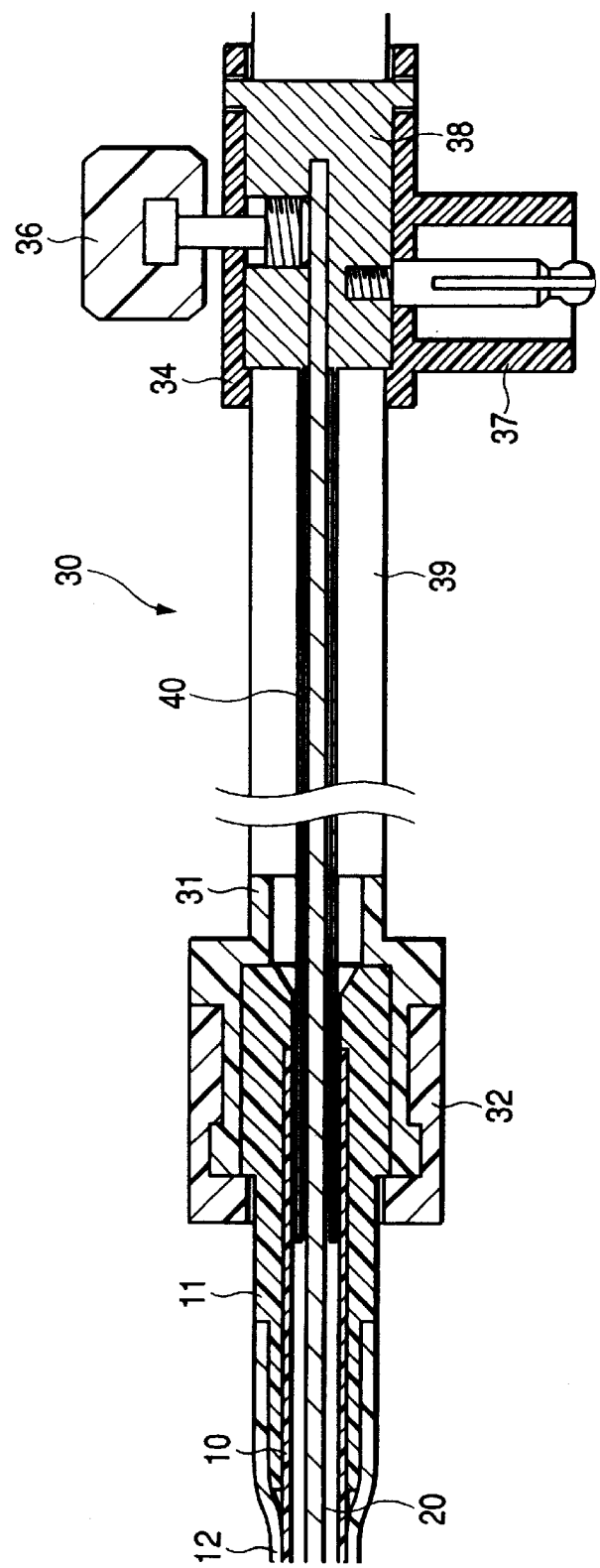
FIG. 1 is a sectional side view of a connecting part in an endoscopic treating instrument according to a first embodiment of the invention.

Now, referring to the drawings, preferred embodiments of the invention will be described.

Figure 2:
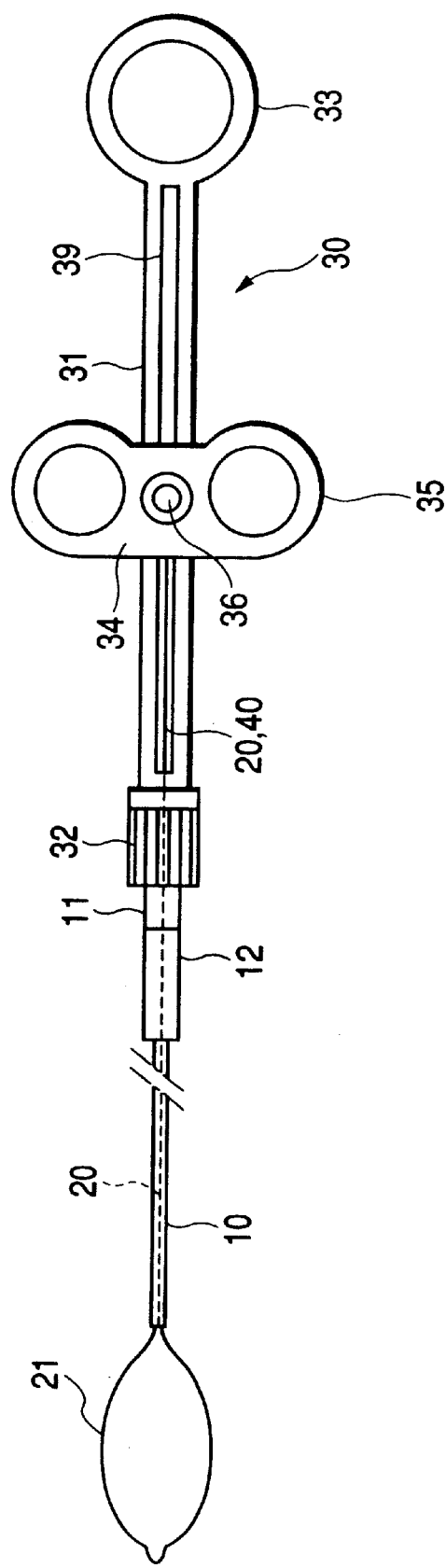
FIG. 2 is a plan view showing an entire structure of the endoscopic treating instrument according to the first embodiment of the invention.

FIG. 2 shows a endoscopic high frequency snare to which the invention is applied. However, the invention can be applied to various types of the endoscopic treating instruments.

A flexible sheath 10 is adapted to be inserted into and removed from a treating instrument insertion channel of an unillustrated endoscope, which is formed, for instance, of a tetra-fluoroethylene resin tube having a diameter of about 2–3 mm and a total length of about 1–2 m.

A sheath base end joint 11 is fixed to a base end of the flexible sheath 10, and detachably connected to an operating section 30. Numeral 32 designates a press ring for manually fixing the sheath base end joint 11 to an operating section main body 31, and numeral 12 designates a bending prevention tube for preventing the base end portion of the flexible sheath 10 from being bent.

An operation wire 20 formed, for instance, of a strand of stainless steel is axially movably passed through the inside of the flexible sheath 10 to extend along the entire length of the sheath 10, and a snare loop 21 is connected to a forward end of the operation wire 20.

The snare loop 21 is adapted to be retracted into and projected from a forward end of the flexible sheath 10 by manipulating the operation wire 20 axially at the operating section 30. The snare loop 21 expands by own elasticity outside the flexible sheath 10, and shrinks by elastic deformation when retracted into the flexible sheath 10.

The operating section 30 has a first finger hook 33 on a rearward end of an elongated operating section main body 31, and a second finger hook 35 on a slider (an operating member) 34 which is attached movably along the operating section main body 31.

A base end of the operation wire 20 is pressed through the slider 34, and fixed thereto by a manually operable wire fixing screw 36, so that the manipulation of the slider 34 causes the operation wire 20 to be axially moved in the flexible sheath 10.

FIG. 1 shows a connecting part of the flexible sheath 10 and the operation wire 20 to the operating section 30. The sheath base end joint 11 is fitted into a fitting hole which is formed at a forward end of the operating section main body 31, and pressed by a press ring 32 so as not to escape from the fitting hole. It is to be noted that, by rotating the press ring 32 about an axis, the sheath base end joint 11 will be put in a condition that it can be removed from the fitting hole in a forward direction (leftward in FIG. 3).

The operating section main body 31 is formed with a slot 39 extending in a longitudinal direction. An electrically conductive block (an operating member) 38 is disposed in the slot 39, and embraced by and engaged with the slider 34. Thus, the electrically conductive block 38 and the slider 34 are moved integrally as a unit.

The base end portion of the operation wire 20 drawn out of the base end of the flexible sheath 10 is passed straightly through the slot 39 and inserted into a hole formed in the electrically conductive block 38, and then, pressingly fixed to the electrically conductive block 38 by the wire fixing screw 36 laterally.

An area adjacent to the base end (for instance, in a range of 1–2 cm from the end) of the operation wire 20 to be pressed by a tip end of the wire fixing screw 36 may be set with silver wax or covered with a metal pipe in order to resist crushing. By preventing the crushing of the end of the operation wire 20 in this manner, the work for passing the operation wire 20 through a reinforcing pipe 40 will become easy at assembling.

Numeral 37 designates a connecting terminal adapted to receive a high frequency electric source cord (not shown). The electrically conductive block 38 is made of an electrically conductive metal and in an electrical communication with the a connecting terminal 37 and the operation wire 20. Accordingly, when the high frequency electric source is connected to the connecting terminal 37, a high frequency electric current is transmitted to the snare loop 21 through the electrically conductive block 38 and the operation wire 20.

In the operating section 30 thus constructed, the reinforcing pipe (a reinforcing cover) 40 made of metal is loosely fitted around the operation wire 20. The reinforcing pipe 40 extends inside the slot 39 to an inlet of the flexible sheath 10 to prevent the operation wire 20 which has been drawn out of the flexible sheath 10 from being bent when the operation wire 20 is inserted into the flexible sheath 40 with manipulation.

One end of the reinforcing pipe 40 is fixedly connected to the electrically conductive block 38. In this embodiment, the reinforcing pipe 40 and the electrically conductive block 38 are formed integrally as a unitary body.

The reinforcing pipe 40 has such a length that its forward end is always located inside the flexible sheath 10 when the slider 34 is manipulated axially. The reinforcing pipe 40 may be formed as a separate part from the electrically conductive block 38 and may be connected and fixed to the electrically conductive block 38 or the slider 34, etc.

Because the base end portion of the operation wire 20 which has drawn out of the base end of the flexible sheath 10 is reinforced by the reinforcing pipe 40 during use, the endoscopic treating instrument according to the embodiment thus constructed will not be subjected to inconveniences such as bending of the operation wire 20 when it is manipulated to be forced into the flexible sheath 10.

After the use, the flexible sheath 10 and the operation wire 20 can be separated from the operating section 30 by loosening the press ring 32 and the wire fixing screw 36. Then, the operation wire 20 can be removed from the flexible sheath 10 so that they are cleaned and sterilized separately.

In reassembling, the operation wire 20 which is not equipped with the reinforcing pipe 40 can be simply inserted into the flexible sheath 10, and so, the work for inserting the operation wire 20 into the flexible sheath 10 can be conducted easily.

Figure 3:
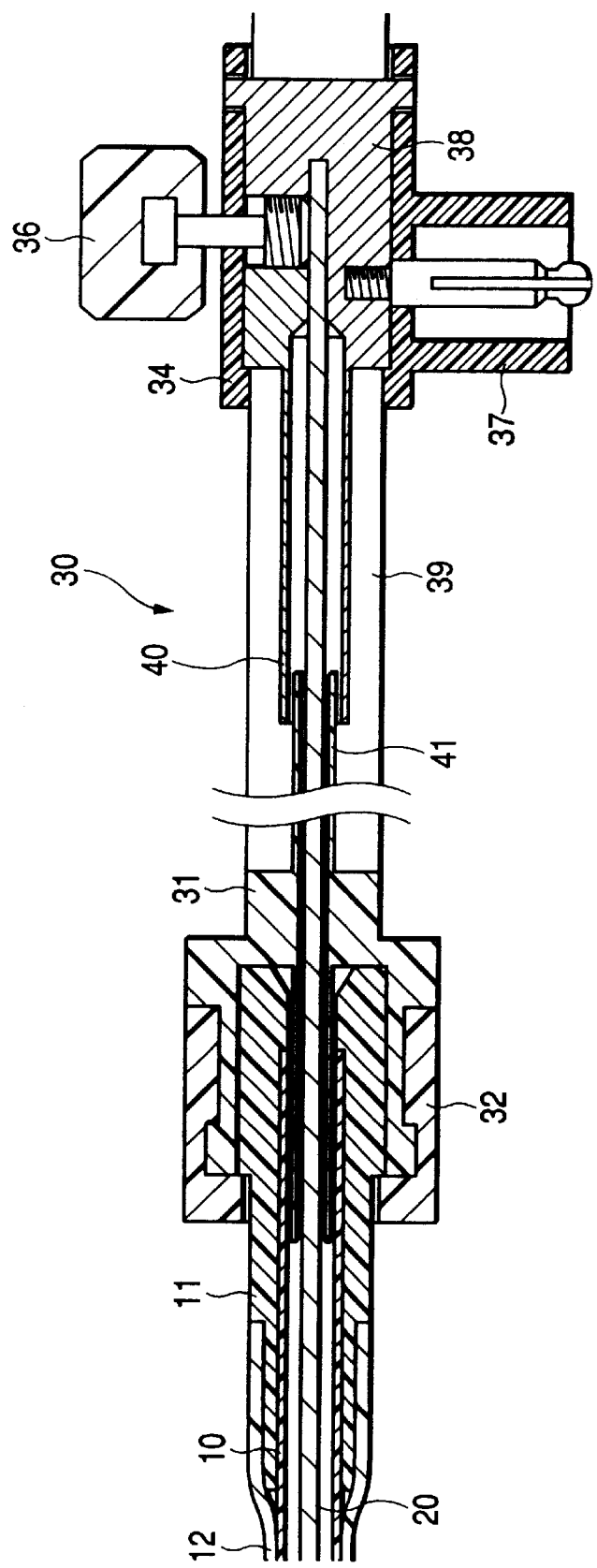
FIG. 3 is a sectional side view of a connecting part in an endoscopic treating instrument according to a second embodiment of the invention.

FIG. 3 shows a connecting part of the flexible sheath 10 and the operation wire 20 to the operating section 30 in a second embodiment according to the invention. In this embodiment, the reinforcing pipe 40 extending from the electrically conductive block 38 is formed shorter than in the above described first embodiment. The remaining portion of the operation wire 20, which is not covered with the first reinforcing pipe 40 is loosely covered with a second reinforcing pipe (a second reinforcing cover) 41 that is provided on the operating section main body 31. Concerning other parts, this embodiment has the same structure as the first embodiment, and has the same function as the first embodiment.

It is to be noted that the invention is not restricted to the above described embodiments. For example, the reinforcing pipe 40 need not be in a form of a pipe, and may take any shape or any member as long as it surrounds the operation wire 20 to restrict the bending of the operation wire 20.

What is claimed is:

1. A connecting part in an endoscopic treating instrument, comprising:
   an operation wire;
   a flexible sheath into which the operation wire is inserted axially movably, the flexible sheath being removable from the operation wire;
   an operating section having a main body to which a base end of the flexible sheath is detachably connected, and an operating member arranged movably with respect to the main body, a base end of the operation wire being detachably connected to the operating member; and
   a reinforcing cover into which the operation wire is loosely inserted and that prevents bending of the operation wire, the reinforcing cover being provided between the base end of the flexible sheath and the operating member and detachable from the operation wire.

2. A connecting part in an endoscopic treating instrument as claimed in claim 1, wherein one end of the reinforcing cover is connected to the operating member.

3. A connecting part in an endoscopic treating instrument as claimed in claim 2, wherein the other, opposite end of the reinforcing cover is located inside the flexible sheath even if the operating member is in a most distanced position from the base end of the flexible sheath.

4. A connecting part in an endoscopic treating instrument as claimed in claim 1, wherein the reinforcing cover includes a first reinforcing cover one end of which is connected to the operating member, and a second reinforcing cover one end of which is connected to the main body.

5. A connecting part in an endoscopic treating instrument as claimed in claim 4, wherein the other, opposite end of the second reinforcing cover is located inside the first reinforcing cover even if the operating member is in a most distanced position from the base end of the flexible sheath.

6. A connecting part in an endoscopic treating instrument as claimed in claim 1, wherein an operating member includes an electrically conductive block and an electrically insulative slider supporting the block, and one end of the reinforcing cover is connected to one of the block and the slider.

7. A connecting part in an endoscopic treating instrument as claimed in claim 6, wherein the reinforcing cover is homogeneously formed as a unitary body with the one of the block and the slider.

* * * * *